United States Patent [19]
Odell et al.

[11] Patent Number: 5,895,386
[45] Date of Patent: Apr. 20, 1999

[54] BIPOLAR COAGULATION APPARATUS AND METHOD FOR ARTHROSCOPY

[75] Inventors: Roger C. Odell, Louisville, Colo.; Joe W. Tippett, San Antonio, Tex.; Lawrence T. Kirwan, Jr., Penbroke, Mass.

[73] Assignee: Electroscope, Inc., Boulder, Colo.

[21] Appl. No.: 08/770,241

[22] Filed: Dec. 20, 1996

[51] Int. Cl.⁶ ................................. A61B 17/39
[52] U.S. Cl. .................... 606/50; 606/42; 606/49
[58] Field of Search ............... 606/41–50; 128/898

[56] References Cited

U.S. PATENT DOCUMENTS

| | | | |
|---|---|---|---|
| Re. 33,925 | 5/1992 | Bales et al. | 606/48 |
| 3,974,833 | 8/1976 | Durden, III | 128/275.1 |
| 4,043,342 | 8/1977 | Morrison, Jr. | 128/303.14 |
| 4,181,131 | 1/1980 | Ogiu | 128/303.15 |
| 4,232,676 | 11/1980 | Herczog | 606/50 |
| 4,427,006 | 1/1984 | Nottke | 128/303.14 |
| 4,562,838 | 1/1986 | Walker | 128/303.14 |
| 4,581,021 | 4/1986 | Landau et al. | 604/212 |
| 4,719,914 | 1/1988 | Johnson | 128/303.3 |
| 4,781,175 | 11/1988 | McGreevy et al. | 128/303.17 |
| 4,787,891 | 11/1988 | Levin et al. | 604/136 |
| 4,800,869 | 1/1989 | Nakajima | 128/4 |
| 4,932,952 | 6/1990 | Wojciechowicz, Jr. | 606/49 |
| 4,998,933 | 3/1991 | Eggers et al. | 606/41 |
| 5,009,656 | 4/1991 | Reimels | 606/48 |
| 5,084,045 | 1/1992 | Helenowski | 606/32 |
| 5,089,002 | 2/1992 | Kirwan, Jr. | 606/50 |
| 5,178,620 | 1/1993 | Eggers et al. | 606/41 |
| 5,277,696 | 1/1994 | Hagen | 606/50 |
| 5,281,216 | 1/1994 | Klicek | 606/42 |
| 5,342,357 | 8/1994 | Nardella | 606/40 |
| 5,366,443 | 11/1994 | Eggers et al. | 604/114 |
| 5,383,876 | 1/1995 | Nardella | 606/50 |
| 5,403,311 | 4/1995 | Abele et al. | 606/48 |
| 5,419,767 | 5/1995 | Eggers et al. | 604/114 |
| 5,423,811 | 6/1995 | Imran et al. | 606/41 |
| 5,520,685 | 5/1996 | Wojciechowicz | 606/49 |
| 5,683,366 | 11/1997 | Eggers et al. | 604/114 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |

*Primary Examiner*—Jack W. Lavinder
*Assistant Examiner*—David M. Ruddy
*Attorney, Agent, or Firm*—James R. Young; Scott B. Allison; Chrisman, Bynum & Johnson, P.C.

[57] ABSTRACT

A bipolar blood coagulator probe has a coaxial or other bipolar arrangement for use submerged in a sterile fluid during arthroscopy of joints, with an elongated outer electrode positioned in juxtaposition to an elongated inner electrode and with an elongated electrical inner insulation layer positioned between the outer electrode and the inner electrode. The outer electrode, inner electric, and inner insulation can be concentric to each other or in other configurations, including sandwiched or laminated together. The bipolar probe also has an elongated outer electrical insulation sleeve over the outer electrode and a proximal end outer housing terminating in a plug with two prongs that are electrically connected in the housing to outer electrode and inner electrode. The prongs of the plug are adapted to plug into a suitable receptacle for connection to an RF generator. The distal ends of the outer electrode, inner insulation layer, and inner electrode of the bipolar probe extend longitudinally a distance beyond the distal end of the outer insulation sleeve to leave a length of exposed surface of the outer electrode. Positioning the surface of the exposed portion of the outer electrode in contact with the tissue near a bleeding blood vessel with the inner electrode a distance spaced away from the tissue in the sterile fluid and applying RF power results in initial coagulation of blood and denaturing of a small amount of surrounding tissue, which is a self-limiting process that prevents excessive necrosis. The probe can also be used with some or all of the distal ends of both of the electrodes or just one of the electrodes in contact with tissue that is submersed in the sterile fluid and is to be necrosed or with blood that is to be coagulated during arthroscopy.

21 Claims, 8 Drawing Sheets

BIPOLAR COAGULATION APPARATUS AND METHOD FOR ARTHROSCOPY

BACKGROUND OF THE INVENTION

1. Field of the Invention

This invention relates to electrosurgical devices and more specifically to bipolar blood coagulation apparatus and method for arthroscopy.

2. State of the Prior Art

Arthroscopic surgery is used to treat: (i) torn menisci, anterior cruciate, posterior cruciate, patella malalignment, synovial diseases, loose bodies, osteal defects, osteophytes, and damaged articular cartilage (chondromalacia) of the knee; (ii) synovial disorders, labial tears, loose bodies, rotator cuff tears, anterior impingement and degenerative joint disease of the acromioclavicular joint and diseased articular cartilage of the shoulder joint; (iii) synovial disorders, loose bodies, osteophytes, and diseased articular cartilage of the elbow joint; (iv) synovial disorder, loose bodies, ligament tears and diseased articular cartilage of the wrist; (v) synovial disorders, loose bodies, labrum tears and diseased articular cartilage in the hip; and (vi) synovial disorders, loose bodies, osteophytes, fractures, and diseased articular cartilage in the ankle. When performing an arthroscopy of the shoulder, elbow, wrist, hip, knee, or ankle involving connective tissue using a rotary shaver, the laceration of blood vessels, such as veins and venuals, arterials and arteries, and capillaries, produces bleeding. Very minor bleeding can be tolerated if the sterile fluid used in arthroscopy flushes the blood away and maintains visibility in the joint. However, if a damaged blood vessel bleeds enough to impair the surgeon's vision in the joint, the bleeding has to be stopped quickly and efficiently to avoid delays or possibly even having to abort the arthroscopic procedure. While it is not desirable, bleeding can be controlled in a knee joint by applying a tourniquet to the thigh above the knee. However, no tourniquet is possible to stop bleeding in the shoulder, and some surgeons would prefer not to use tourniquets in arthroscopy of other joints, such as elbows, wrists, hips, knees, and ankles, if bleeding can be controlled in other ways. Also, excessive bleeding can cause the surgeon to have to provide a temporary drain in the joint for post surgery draining of excessive blood accumulation in the joint.

The most common method of controlling bleeding blood vessels, "bleeders," in arthroscopic procedures in shoulders and in other joints when tourniquets are not possible or desirable is to use a monopolar electrosurgical probe to coagulate or cauterize the bleeding blood vessel. A typical monopolar electrosurgical device utilizes a monopolar probe for one electric pole and a large area plate in contact with the patent's skin at a location remote from the arthroscopic surgery, such as the patient's back, for the other electric pole. Both the probe and the plate are connected electrically to a radio frequency (RF) generator. When the tip of the monopolar probe is positioned adjacent or touching the connective tissue and the RF electrical power is turned on, the person's body completes the electric circuit between the monopolar probe and the large area plate, and electric current flows through the patient's body between the monopolar probe and the plate. When enough current and voltage is applied, the tissue where the current is flowing will get hot and result in hemostasis (stopping the flow of blood) and necrosis (pathologic death of cells) of the surrounding tissue. Since the plate is in contact with a much larger surface area of the body than the monopolar probe, the density or concentration of the electric current flowing through the body tissue is greater at the probe than at the plate. Therefore, the tissue adjacent the monopolar probe becomes hotter than the tissue adjacent the plate, and the heat produced where the monopolar probe contacts the tissue where the bleeding occurs causes coagulation resulting in hemostasis (stemming flow of blood). In addition, normal tissue adjacent the probe contact point becomes denatured and damaged by the heat produced by electric current flowing through the tissue near the probe during this coagulation method. Therefore, when the monopolar probe is positioned on the tissue surrounding the bleeder, or on the bleeding blood vessel itself, the RF current will cause denaturing and necrosis at the target site as well as of the surrounding tissue. Since the electric current flows through the body tissue between the monopolar probe and the remotely located plate, the depth and volume of necrosis is indefinite and difficult to control, but can easily extend, for example, to over one centimeter wide and over one-half centimeter deep in a typical operation to stop a bleeder, but it will continue to extend even deeper as long as the monopolar probe is held in contact with the tissue while the power is turned on. While such monopolar coagulation is effective to stop the bleeding, it also denatures a considerable amount of surrounding tissue, thus necrosing more of the normal surrounding connective tissue in the joint than is strictly needed or desired.

The bipolar coagulator disclosed in U.S. Pat. No. 5,089,002, issued in 1992 to Lawrence T. Kirwan, Jr., one of the co-inventors of this invention, and which is incorporated herein by reference, is a bipolar device that was designed for desiccating several microscopic layers of eye tissue, including tiny blood vessels, on the eye before eye surgery in order to reduce bleeding encounters during eye surgery. The result is that the tiny blood vessels near the eye surface, where the surgical incisions are to be made during eye surgery, are necrosed—virtually obliterated or erased—before any incisions are made. A bipolar coagulator similar to that shown and described in U.S. Pat. No. 5,089,002, but with an electrical insulation coating around substantially the entire length of the outer conductor or electrode, was also developed by Lawrence T. Kirwan, Jr., for very fine hemotosis in neural endoscopy applications where the insulation coating prevents outer electrode contact with surrounding tissue. However, both of those bipolar coagulators developed by Kirwan are designed for the specific eye surgery and neural endoscopy necrosing applications described above, which are not in fluid-filled environments and which are not effective for coagulating bleeders encountered in the arthroscopy procedures described above.

SUMMARY OF THE INVENTION

Accordingly, it is a general object of the present invention to provide an electrosurgical probe that is effective for coagulating bleeding blood vessels in connective tissue that are damaged during arthroscopy of joints, including shoulder, elbow, wrist, hip, knee, and ankle joints in a fluid filled medium.

A more specific object of this invention is to provide a probe that coagulates bleeders in arthroscopic surgery effectively and efficiently while minimizing tissue necrosis surrounding the bleeders.

Another object of this invention is to provide an alternative method and apparatus to control bleeders in arthroscopy of elbow, wrist, knee, and ankle joints when surgeons elect not to use tourniquets.

A further object of this invention is to provide a method and apparatus that provides sufficiently effective hemostasis of bleeders in arthroscopy that may enable a surgeon at least in some circumstances to elect not to use post surgery drain.

A still further object of this invention is to provide a coagulation probe that can be used in a variety of joints and in a variety of positions in arthroscopy procedures.

Yet another object of the present invention is to provide an electrosurgical probe for coagulating blood vessels that is reusable and disposable.

Additional objects, advantages, and novel features of the invention are set forth in part in the description that follows, and in part will become apparent to those skilled in the art upon examination of the following description or may be learned by the practice of the invention. The objects and the advantages may be realized and attained by means of the instrumentalities and in combinations particularly pointed out in the appended claims.

To achieve the foregoing and other objects and in accordance with the purposes of the present invention, as embodied and broadly described herein, the bipolar coagulation apparatus of this invention may comprise an elongated co-axial probe including an elongated inner electrode surrounded by an elongated outer electrode with a layer of electrical insulation positioned between the inner electrode and the outer electrode. A sleeve of electrical insulative material surrounds the outer electrode for most, but not all of the length of the outer electrode. Distal ends of both the inner electrode and the outer electrode are not covered with electrical insulative material.

To achieve the foregoing and other objects and in accordance with the purposes of the present invention, as embodied and broadly described herein, the method of this invention may comprise positioning a peripheral surface of a first electrode into a saline fluid, preferably a normal saline fluid, and in contact with connective tissue, positioning a second electrode in the saline fluid adjacent the bleeder but a spaced distance outwardly from the connective tissue, and applying an RF electric current through the first electrode and the second electrode while applying a voltage across the first electrode and the second electrode.

BRIEF DESCRIPTION OF THE DRAWINGS

The accompanying drawings, which are incorporated in and form a part of the specifications, illustrate the preferred embodiments of the present invention, and together with the descriptions serve to explain the principles of the invention. In the Drawings.

DETAILED DESCRIPTION OF THE PREFERRED EMBODIMENT

Figure 1:
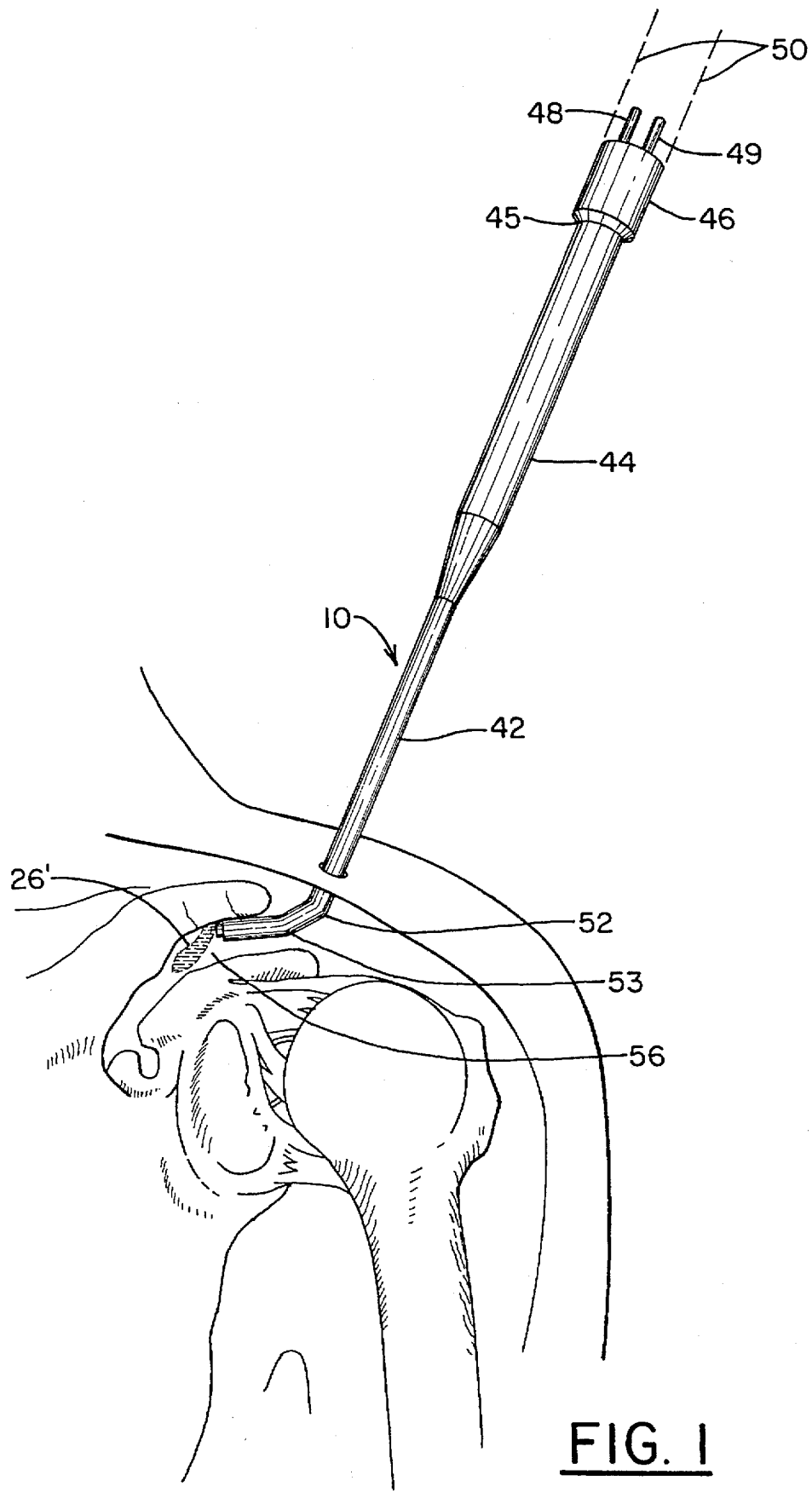
FIG. 1 is a perspective view showing the bipolar probe device of the present invention in position to coagulate and stop a flow of blood from a damaged blood vessel in an exemplary arthroscopic procedure in the subacromial space of a shoulder.
Figure 2:
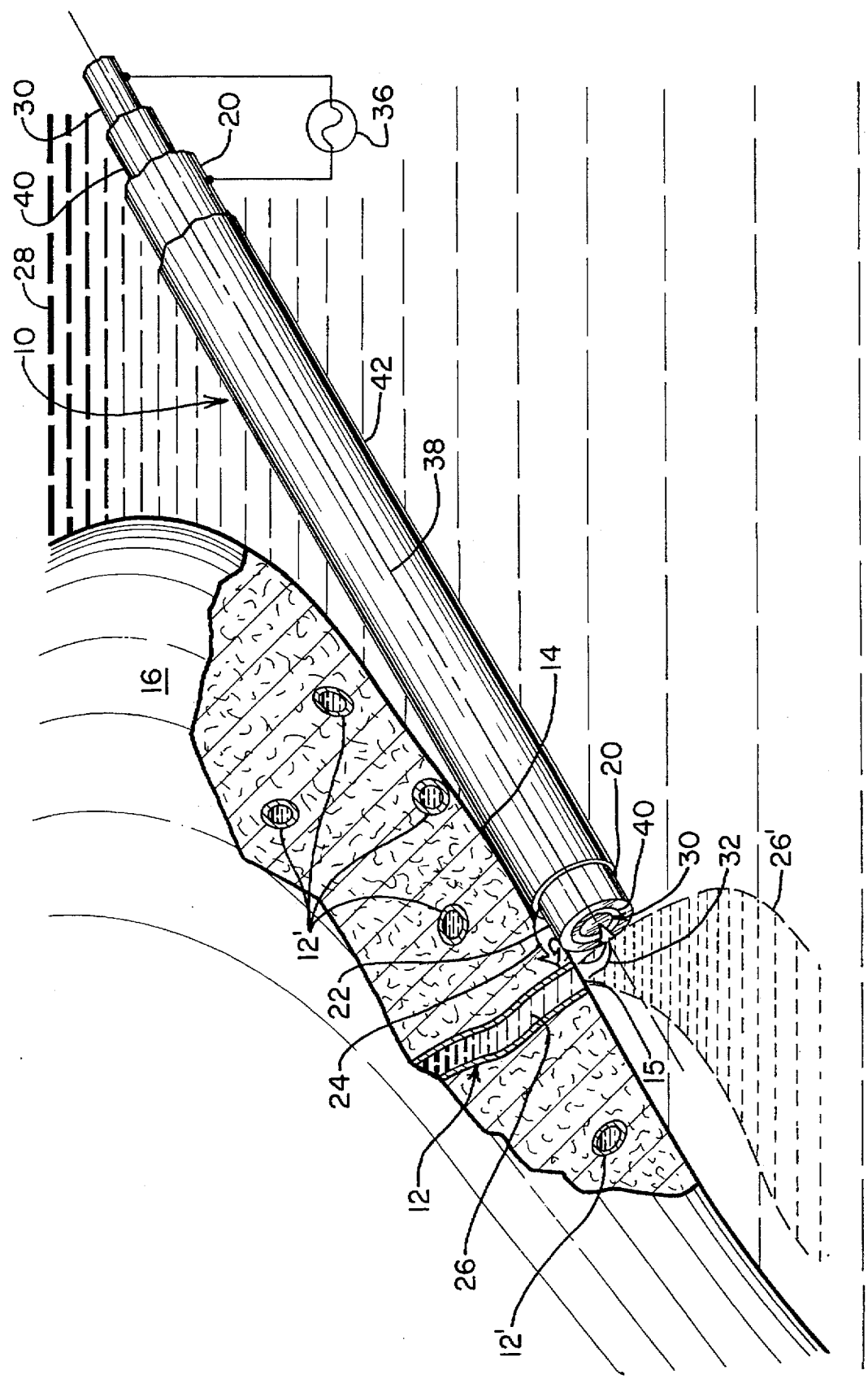
FIG. 2 is an enlarged isometric view of the distal end of the bipolar coagulation probe of this invention positioned adjacent a bleeding blood vessel or "bleeder" in a section of connective tissue that is undergoing arthroscopy, a portion of which tissue is illustrated in cross-section to show the damaged and bleeding blood vessel more clearly, and illustrating current flow through the adjacent tissue, blood, and immersing sterile fluid.

The bipolar coagulation probe 10 of the present invention is illustrated in FIG. 1 in a typical application of coagulating and stemming the flow of blood 26' from a damaged and bleeding blood vessel during arthroscopic surgery in the subacromial space 56 of a shoulder, although it can also be used in much the same way in the intra-articular spaces in shoulders and knees as well as in elbows, wrists, hips, and ankles. An enlarged view of the distal portion of the bipolar coagulation probe 10 of the present invention is shown in FIG. 2 positioned adjacent a damaged and bleeding blood vessel 12 at the exposed surface 14 of a layer of connective tissue 16, such as, for example but not for limitation, the subacromial space 56 in the shoulder. The damaged blood vessel 12 may be any one of many blood vessels 12' in the connective tissue 16 and, for purposes of illustration and explanation of this invention, has been cut or ruptured by a rotary shaver (not shown) or other tool used by an orthopedic surgeon to ablate (remove) chondromalacia (damaged, worn, or diseased cartilage) or to remove connective tissue during arthroscopy. The probe is shown immersed in a sterile fluid 28, which is injected into and flows through the subacromial space 56 during arthroscopy to expand the surrounding tissue (not shown in FIG. 2) and clear debris (not shown) created by the surgical procedure and to keep the surgeon's field of vision into the space clear. The sterile fluid 28 is preferably a normal saline, ringer lactate, or other fluid used in arthroscopic surgery. The blood 26 is shown in FIG. 2 flowing out of the damaged or severed end or "bleeding area" 15 of the blood vessel 12 into the sterile fluid 28, where it forms a plume of blood 26' diluted by the sterile fluid 28.

In operation, the exposed peripheral surface 22 of the outer electrode 20 at the distal end of the probe 10 is positioned in contact with the exposed surface 14 of the connective tissue 16 adjacent the damaged blood vessel or "bleeder" 12. The RF electric power source indicated diagrammatically at 36 is turned on causing RF current to flow, as indicated by arrow 24, through the portion of the connective tissue 16 that is in contact with the outer electrode 20 and, as indicated by arrow 32, through the blood 26 that is in the damaged end of the blood vessel 12 and that is escaping from the damaged blood vessel 12 into the sterile fluid 28 and to the inner electrode 30. Actually, the current is an RF (radio frequency) alternating current, so it flows in both directions, but the arrows 24, 32, while not strictly technically accurate, do depict in a simplified diagrammatic manner the current path through the connective tissue 16 and blood 26 between the outer electrode 20 and the inner electrode 30 in a sufficient manner to describe the invention, as will be understood by persons skilled in the art. The electric current flowing through the blood 26, as indicated by arrow 32, heats the blood 26 to a sufficient extent to cause coagulation to stop the bleeding from the damaged blood vessel 12, as will be explained in more detail below.

An important feature of this invention is the biophysics, i.e., self-selectivity, of the current path 24, 32 initially between the outer electrode 20 and the inner electrode 30, as described above, and then self-limiting the current flowing in the connective tissue 16 and diverting to an alternate path to flow predominately directly from the outer electrode 20 through the sterile fluid 28 to the inner electrode 30, as will also be described in more detail below.

The overall structure of the probe 10 is similar to the structure described in U.S. Pat. No. 5,089,002, which is incorporated herein by reference, but with several significant differences that are explained below. Similar to that structure, the probe 10 of this invention preferably has a coaxial bipolar arrangement with the elongated outer electrode 20 positioned preferably concentrically around the elongated inner electrode 30 and with an elongated concentric electrical inner insulation layer 40 positioned between the outer electrode 20 and the inner electrode 30. Portions of the outer electrode 20 and the inner insulation layer 40 adjacent their respective distal ends 21, 41 are shown cut away in FIG. 3 to reveal this structure more clearly. The proximal end 45 of outer housing 44 terminates in a plug 46 with two prongs 48, 49, as shown in FIG. 1, that are electrically connected (not shown) in the housing 44 to the outer electrode 20 and inner electrode 30, respectively. The prongs 48, 49 of the plug 46 are adapted to plug into a suitable receptacle indicated only by phantom lines 50 in FIG. 1, which, as will be understood by persons skilled in the art, could be a conventional connection to an RF generator 36, which is denoted only schematically in FIGS. 2–5. Unlike the structure in U.S. Pat. No. 5,089,002, however, the probe 10 of this invention has an elongated outer electrical insulation sleeve 42 concentrically around the outer electrode 20, as shown in FIGS. 1–5.

The distal ends 21, 41, 31 of the outer electrode 20, inner insulation layer 40, and inner electrode 30, respectively, of the probe 10 of the present invention extend longitudinally a distance beyond the distal end 43 of the outer insulation sleeve 42 to leave a length of exposed peripheral surface 22 of the outer electrode 20, as best seen in FIGS. 2–5. This length of exposed peripheral surface 22 of outer electrode 20 provides the ability to make a substantial sized electrical contact between the connective tissue 16 and the outer electrode 20 adjacent a bleeder 12 while maintaining the inner electrode 30 spaced a small distance away from the connective tissue 16 so that the electric current path to the inner electrode 30 is completed by the sterile fluid 28 and/or the flowing blood 26, as described above. Such electrical contact is preferably, but not necessarily, made with this structure by placing the exposed peripheral surface 22 substantially tangential to, and in contact with, the exposed surface 14 of the connective tissue 16, as illustrated in FIGS. 1–5. Also, while not essential, it is preferable to terminate the distal ends 21, 31, 41 of the outer electrode 20, inner electrode 30, and inner insulation layer 40, respectively, substantially in a common plane perpendicular to the longitudinal axis 38 of the probe 10, as illustrated in FIGS. 2–5, although the inner electrode 30 could protrude longitudinally slightly beyond the outer electrode 20. With this configuration, there is no rotationally preferred orientation of the probe 10 with respect to the connective tissue 16 or with respect to the bleeder 12. It is also preferred, although not essential, that the outer electrode 20 and inner electrode 30 be made of a malleable metal or alloy, for example aluminum, which can be easily formed or bent into any desired shape or configuration to enable ready access and optimum positioning of the probe tip 10 in places that are tight or difficult to reach, as illustrated in FIG. 1. The inner insulation layer 40 and outer insulation sleeve 42 can be any of a variety of high temperature, flexible plastics, such as, for example, poly vinylidene flouride (PVDF), silicone rubber, tetrafluorethylene (Teflon™), poly ether ether ketone (PEEK), or perfluoralkoxy (PFA), as is understood by persons skilled in the art. For example, as illustrated in FIG. 1, the probe 10 of this invention is particularly suited for use in coagulating bleeders encountered during arthroscopy in the intra-articular and sub-acromial spaces in shoulder joints and in the intra-articular spaces in knee joints, although it can also be used in similar applications to coagulate bleeders in shoulders, elbows, wrists, hips, knees, and ankles. As shown in FIG. 1, the malleable probe 10, as described above, is curved at 52 and 53 to enhance access and optimal positioning in the subacromial space 56 in the shoulder. Again, the probe 10 being malleable, as described above, enables the surgeon to shape and reshape the probe 10 readily and easily to any desired configuration.

Figure 3:
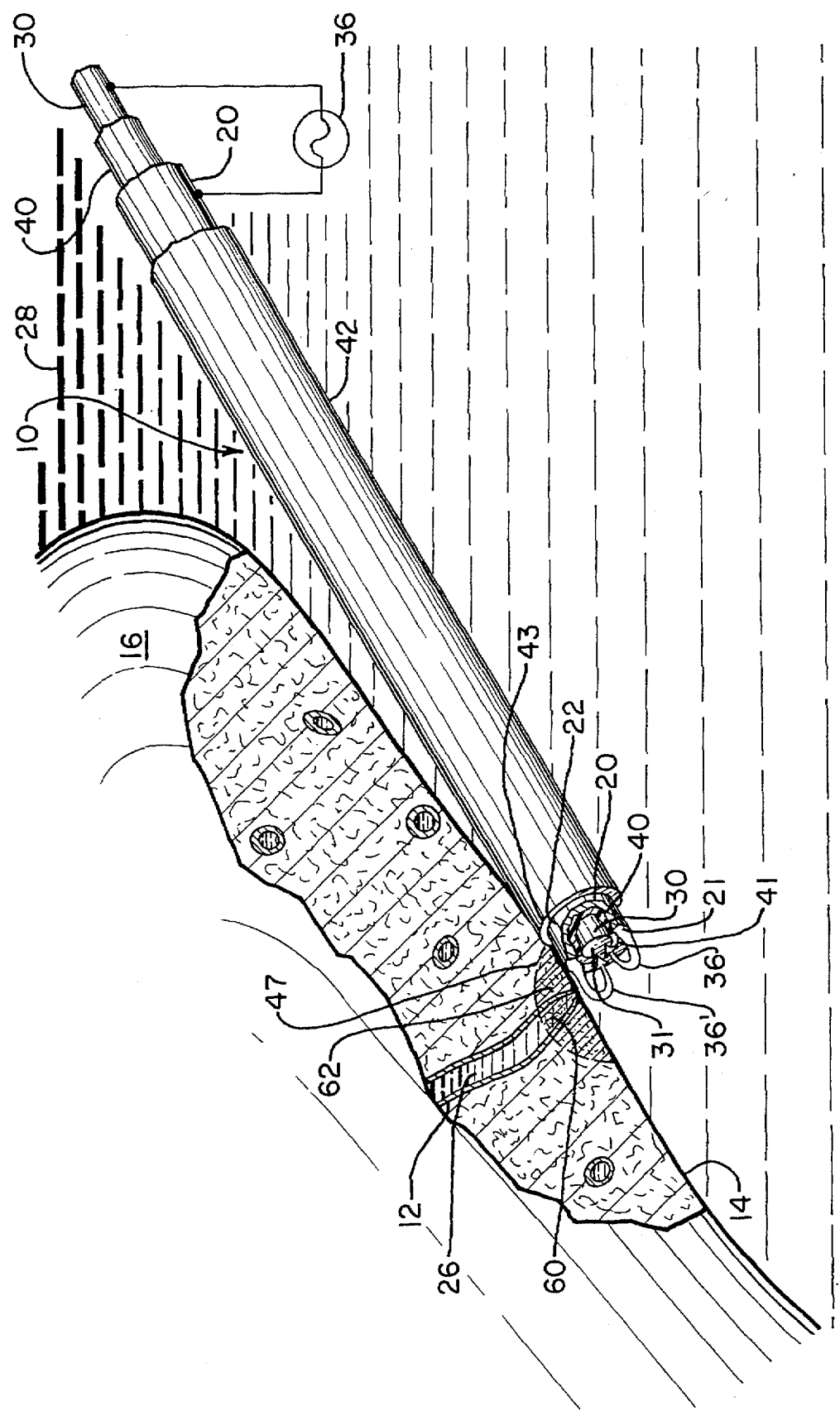
FIG. 3 is an isometric view similar to FIG. 2, but illustrating a coagulated blood vessel and the resulting current flow through the sterile fluid after coagulation is accomplished.

Referring now to FIGS. 2 and 3, the sterile fluid solution 28 is preferably a normal saline fluid, so it will conduct electric current. It is preferred, although not essential, that the blood 26 has an electrolyte density about the same as, or even slightly higher than, the normal saline fluid 28 so that the blood is as conductive as, and possibly slightly more conductive than, the normal saline fluid 28. The blood 26 is also usually more conductive than the surrounding connective tissue 16. Since the electric current will find paths of least resistance to flow between the outer electrode 20 and the inner electrode 30, and since the outer electrode 20 and inner electrode 30 are both positioned adjacent the bleeder 12, a substantial portion of the electric current will flow initially through the bleeding area 15. That current path through the bleeding area 15 requires at least some of the current to flow through the small portion of connective tissue 16 that is between the outer electrode 24 and blood vessel 12, as indicated by arrow 24. Power is the product of the square of the current I times the resistance R, i.e., $I^2R$, so that power is dissipated in the blood 26 at and near the bleeding area 15, where the current is most concentrated and in the small portion of the surrounding connective tissue 16 between the outer electrode 24 and the blood vessel 12. Power dissipates in the form of heat. Consequently, heat is created by the RF current in the blood 26 sufficient to coagulate the blood 26 in blood vessel 12, contact the wall 15 of the blood vessel at the bleed point 13, and denature a small amount of connective tissue 62 surrounding the blood vessel 12 adjacent the bleeding area 15, all as illustrated in FIG. 3. Such coagulation 60 and necrosis of tissue 62 stops the flow of blood 26 from the blood vessel 12.

When coagulation 60 occurs, the blood cells are converted into a dry, dull, fairly homogenous eosinophilic mass that no longer conducts electricity as well as did the liquid blood 26. The small portion of denatured connective tissue 35 is also a dried mass of necrosed cells that also does not conduct electricity as well as did the healthy connective tissue cells. Therefore, the previously described current path 24 in FIG. 2 through the connective tissue 16 becomes one of increased resistance. Consequently the dominate current path changes to flow directly through the sterile fluid 28 between the outer electrode 20 and the inner electrode 30, as indicated diagrammatically by arrows 36 in FIG. 3. Therefore, the previous current flow 24 through connective tissue 16 is self-limiting to coincide with coagulation 34 of the blood 26 at the bleeding area 15, which avoids unnecessary heating and tissue necrosis in the connective tissue 16 or damage to other blood vessels 12' in the proximity, but which are not bleeding, even if the probe 10 is held in the same position with the RF electric power turned on after coagulation 60 occurs.

Figure 4:
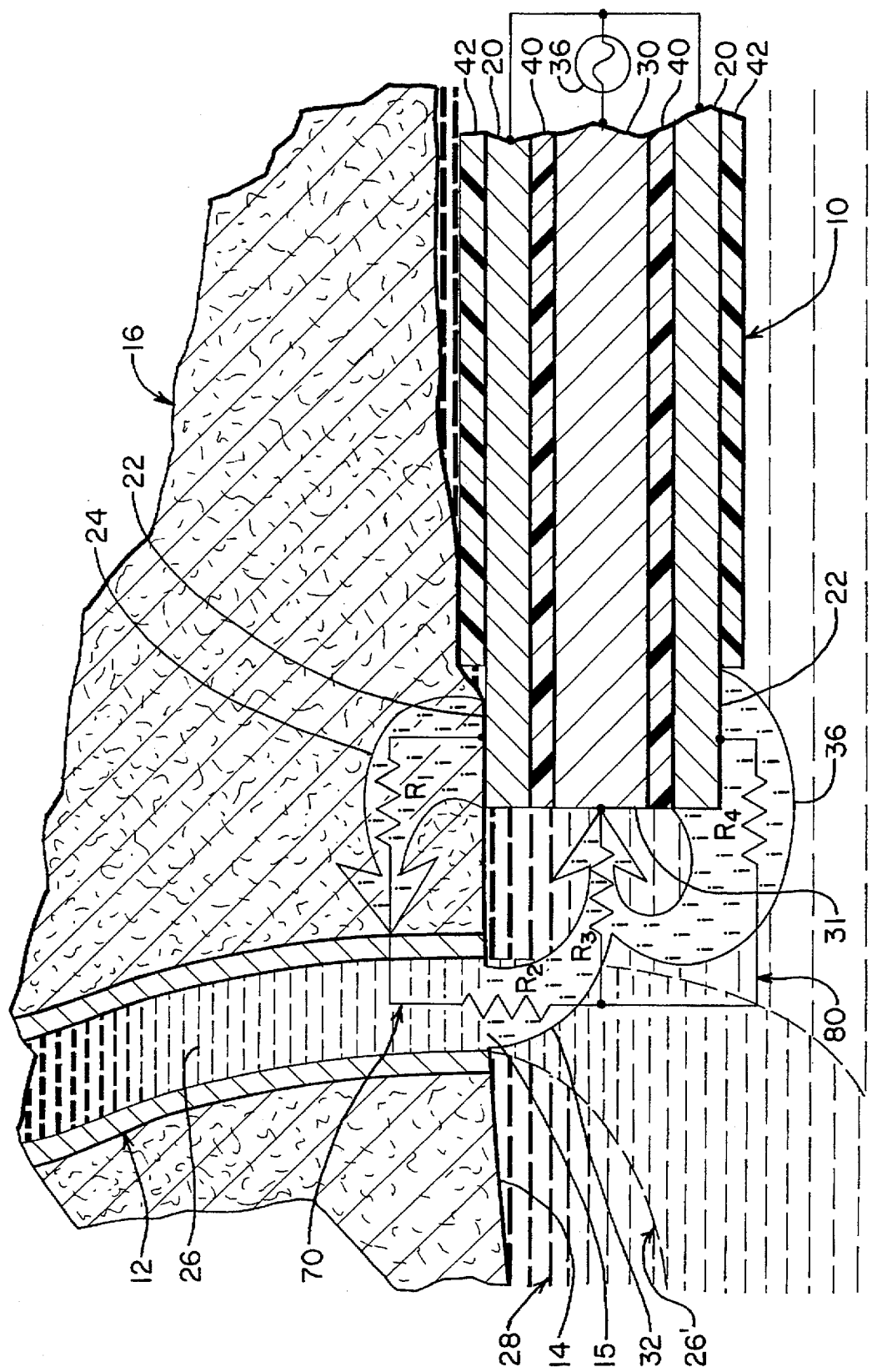
FIG. 4 is an enlarged view in cross-section of the bipolar probe of the present invention being used to coagulate a bleeder in connective tissue with model electrical parallel circuit superimposed to illustrate the operation of the probe according to this invention during coagulation.

This bipolar coagulation probe 10 and its biophysical operation can be modeled and described as two parallel electric circuits 70, 80, as illustrated diagrammatically in FIG. 4. The first parallel circuit 70 extends generally from the portion of the peripheral surface 22 of outer conductor 20 that is in contact with the connective tissue 16 (i) through the small portion of connective tissue 16 that is between the peripheral surface 22 and the damaged blood vessel 12, represented electrically by the resistor $R_1$, (ii) through the blood 26 at and near the bleed area 15, represented electrically by the resistor $R_2$, and (iii) through the portion of the sterile fluid 28 that is between the diluted blood 26' and the distal end 31 of the center electrode 30, represented electrically by the resistor $R_3$. The second parallel circuit 80 extends generally from the portion of the peripheral surface 22 that is in contact with the sterile fluid 28 (i) through the sterile fluid 28, represented electrically by resistor $R_4$, and (ii) through the sterile fluid 28 that is in contact with the distal end 31 of the center electrode 30, represented by the resistor $R_3$. Of course, the parallel circuits 70, 80 described above provide only a simplified electrical model which could have many variations, because the electric currents in this fluid and tissue environment can flow in indefinite variations, depending on many variables, including, but not limited to, relative conductivities of tissue 16, blood 26, diluted blood 26', and sterile fluid 28, as well as relative positions and spacings between the probe 10, blood vessel 12, plume of diluted blood 26', and the like. For example, if the plume of diluted blood 26' is close enough to the probe 10, another resistor (not shown) could be included in the second parallel circuit 80 to represent current flow in the second circuit 80 through the diluted blood 26'. On the other hand, if the probe 10 would be positioned in the flowing sterile fluid 28 downstream of the bleed area 15 so that the plume of diluted blood 26' washes over the distal end of the probe 10, then the resistor $R_3$ may not be significant. However, such resistances in each circuit 70, 80 are additive within each respective circuits 78, 80, so the schematic electrical model shown in FIG. 4, while relatively simple, is adequate for purposes of describing the operation and significant features of this invention, which may include such variations.

As discussed above, a significant advantage of the bipolar probe 10 of the present invention is that it functions very well in arthroscopy, which previously known bipolar probes are incapable of doing, and the resulting volume of necrosis is significantly smaller than would be possible with a monopolar probe 37. Now referring to FIG. 4, the bipolar probe 10 is positioned adjacent the bleeder 12 preferably with a portion of the exposed peripheral surface 22 of the outer electrode 20 in contact with a sufficient area of connective tissue 16 so that electric current flows as indicated by the arrows 24, 32, as described above, but with the distal end 31 of the inner electrode 30 preferably spaced a distance away from the tissue 16 and bleed area 15. It is preferred that the surgeon press the exposed surface 22 of outer electrode 20 into the tissue 16 enough to get a large enough contact area between the outer probe 20 and the tissue 16 to keep the current density in the contact area low enough to keep the temperature of the tissue 16 at the contact area under 100° C., so it does not vaporize. Yet, the exposed surface 22 is not so large that the current density is insufficient to heat the tissue above 50° C., where tissue effects or surgical activity, such as desiccation and blood coagulation, begins. Initially, therefore, a substantial amount of electric current flows through the tissue 16 represented by $R_1$, the blood 12 in bleed area 15 represented by $R_2$, and the sterile fluid 28 represented by $R_3$ in the first parallel circuit 70. At the same time, there will most likely be at least some electric current flowing in the sterile fluid 28, as indicated by arrow 36 and represented by resistors $R_4$ and $R_3$ in the second parallel circuit 80. It is believed, based on observation of the bipolar probe 10 in operation according to this invention, that the blood 12 and possibly also the tissue 16 is less resistive to flow of electric current than the sterile fluid 28 so that the combination of $R_1$ and $R_2$ is less than $R_4$, or at least not substantially greater than $R_4$. Therefore, it is believed that at least as much and possibly more of the electric current flowing between the other electrode 20 and the inner electrode 30 flows in the first parallel circuit 70 of the tissue 16 ($R_1$) and blood 26 ($R_2$) as compared to the second parallel circuit 80 of the sterile fluid 28 ($R_4$). However, it is not necessary that current flows through the tissue 16, blood 26, and sterile fluid 28 for this invention to work. Regardless of the relative proportions, there is sufficient flow of electric current in the first parallel circuit 70 to cause coagulation of the blood 12 and denaturing of the tissue 16 in the area in and immediately surrounding the bleeding area 15 from the heat produced by that electric current flowing through the resistance $R_1$ (tissue) and resistance $R_2$ (blood). There is, of course, also heat produced by the electric currents flowing in both the resistances $R_3$ and $R_4$ (sterile fluid), but the sterile fluid 28 in arthroscopic procedures is kept flowing at a fairly high rate through the area where the procedure is being performed, so heat produced in the sterile fluid 28 (resistances $R_3$ and $R_4$) is carried away and dissipated rapidly by the flowing fluid 28 with no appreciable temperature increase at the probe 10.

Figure 5:
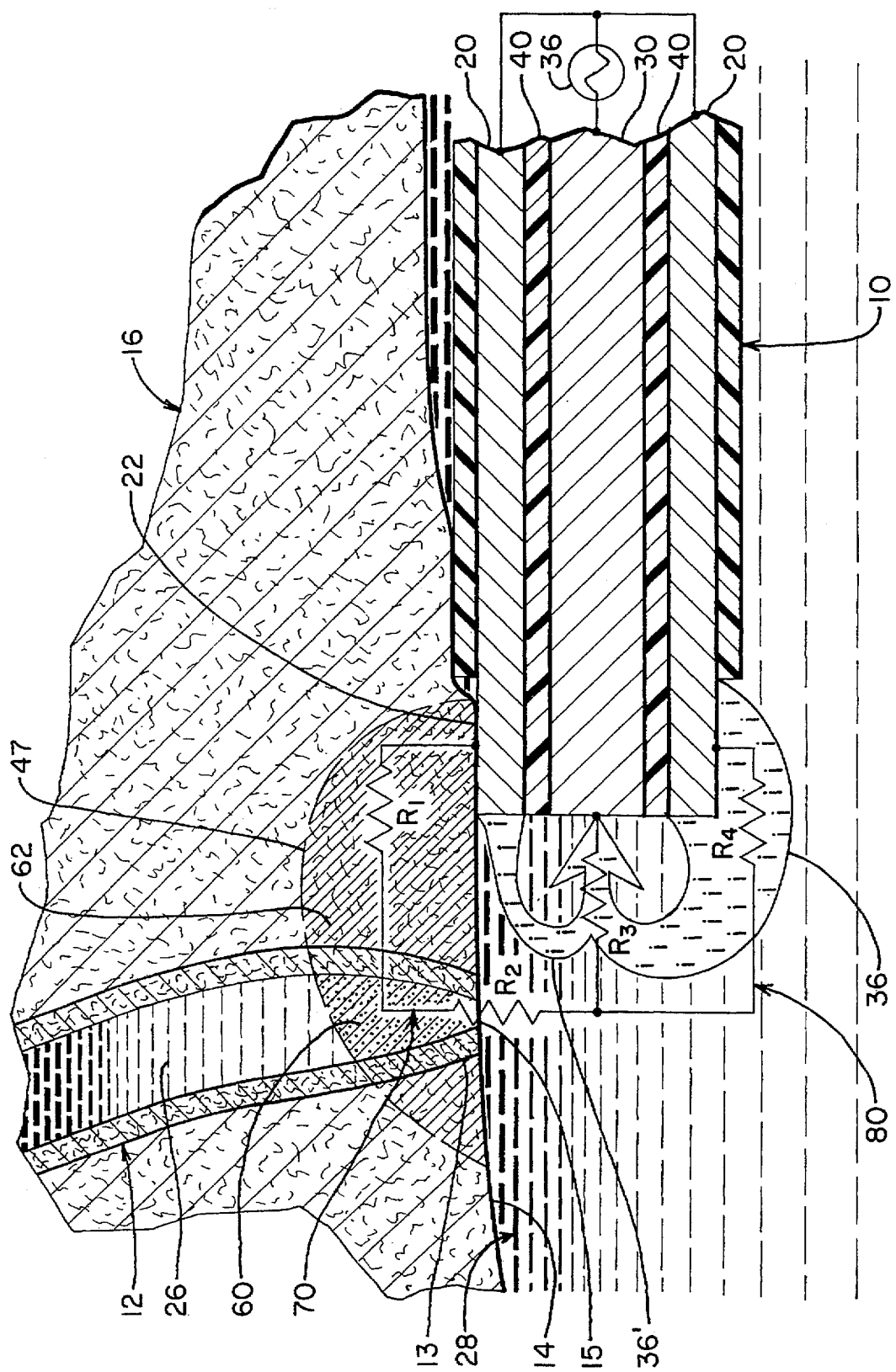
FIG. 5 is an enlarged view in cross-section similar to FIG. 5, but illustrating the self-limiting feature of this invention after coagulation has been accomplished.

The result of the heat produced in the blood 12 and the immediately surrounding tissue 16 as mentioned above, however, is more significant, as illustrated diagrammatically in FIG. 5. As mentioned above, heat causes blood 26 to coagulate and tissue to denature resulting in necrosis by desiccation, i.e., driving water out of the blood and tissue cells, thus destroying the vital processes including enzymes that would otherwise continue to alter the devitalized cellular substance. Coagulated blood cells become a dry, dull, fairly homogenous cosiniphilic mass. Dried and denatured blood vessel tissue shrinks and hardens. Other tissues, such as connective tissues, cartilage, and the like become dried, hardened masses from the heat. Consequently, the heat produced by the electric current flowing through the tissues and blood of the first parallel circuit 70 desiccate or dry the cellular structure of the adjacent end portion 13 of the blood vessel 12 causing it to shrink, as illustrated in FIG. 5, to at least partially close the damaged or severed blood vessel 12. At the same time, the heat produced by the current flowing in the bleeding area 15 coagulates the blood 26 in the end portion 13 of the blood vessel 12 to form a plug of coagulated blood 60. The combination of the coagulated blood plug 60 with the shrunken end portion 13 of the blood vessel 12 effectively stems the flow of blood 26 from the blood vessel 12, as illustrated in FIG. 5. The heat produced by electric current flowing through tissue 16 causes a small amount of necrosed tissue 62 around the end 13 of blood vessel 12, as also illustrated in FIG. 5.

However, the coagulated plug 60 and the necrosed tissue 62, which comprise desiccated (dried) cell masses, do not conduct electricity nearly as well as the blood 26 and tissue 16 did or nearly as well as the sterile fluid 28 does. Therefore, as the necrosis 62 and the coagulated plug 60 form, the respective resistances $R_1$ and $R_2$ increase until current flow in the first parallel circuit 70 virtually stops, and virtually all of the current flow between the outer conductor 20 and the inner conductor 30 shifts automatically to the second parallel circuit 80 through the sterile fluid 28, as indicated by arrows 36, 36' in FIG. 5, where resistance $R_4$ remains substantially unchanged. Of course, as current flow through the tissue 16 and blood 26 stops, heat production in tissue 16 and blood 26 also stops. Therefore, denaturing and coagulating heat in tissue 16 and blood 26 only migrates a small distance into the tissue 16 and blood vessel 12, as indicated by the boundary line 47 in FIG. 5, before the current flow shifts away from the tissue 16 and blood 26 path of the first parallel circuit 70 almost entirely to the sterile fluid 28 path of the second parallel circuit 80. Thereafter, no further heat, thus no further necrosis of tissue 16 or coagulation of blood 26 occurs, regardless of how long the probe 10 remains in that position with the power turned on. This self-limiting feature of this invention, in which the initial denaturing of tissue 16 and coagulation of blood 26 results in increased resistance and stopping the heat-producing flow of electric current through the tissue 16 and blood 26, diverting the electric current flow instead almost entirely to the second parallel circuit 80 of the sterile fluid, allows fast and effective stemming of bleeders, but also prevents excessive and unnecessarily deep necrosis of tissue 16. It also allows enough heat to desiccate or dry the tissue cells, but stops the electric current, thus heat production, before cell vaporization occurs. For example, the volume of necrosis for the bipolar probe 10 according to this invention may be only about three millimeters deep and three millimeters wide.

Figure 6:
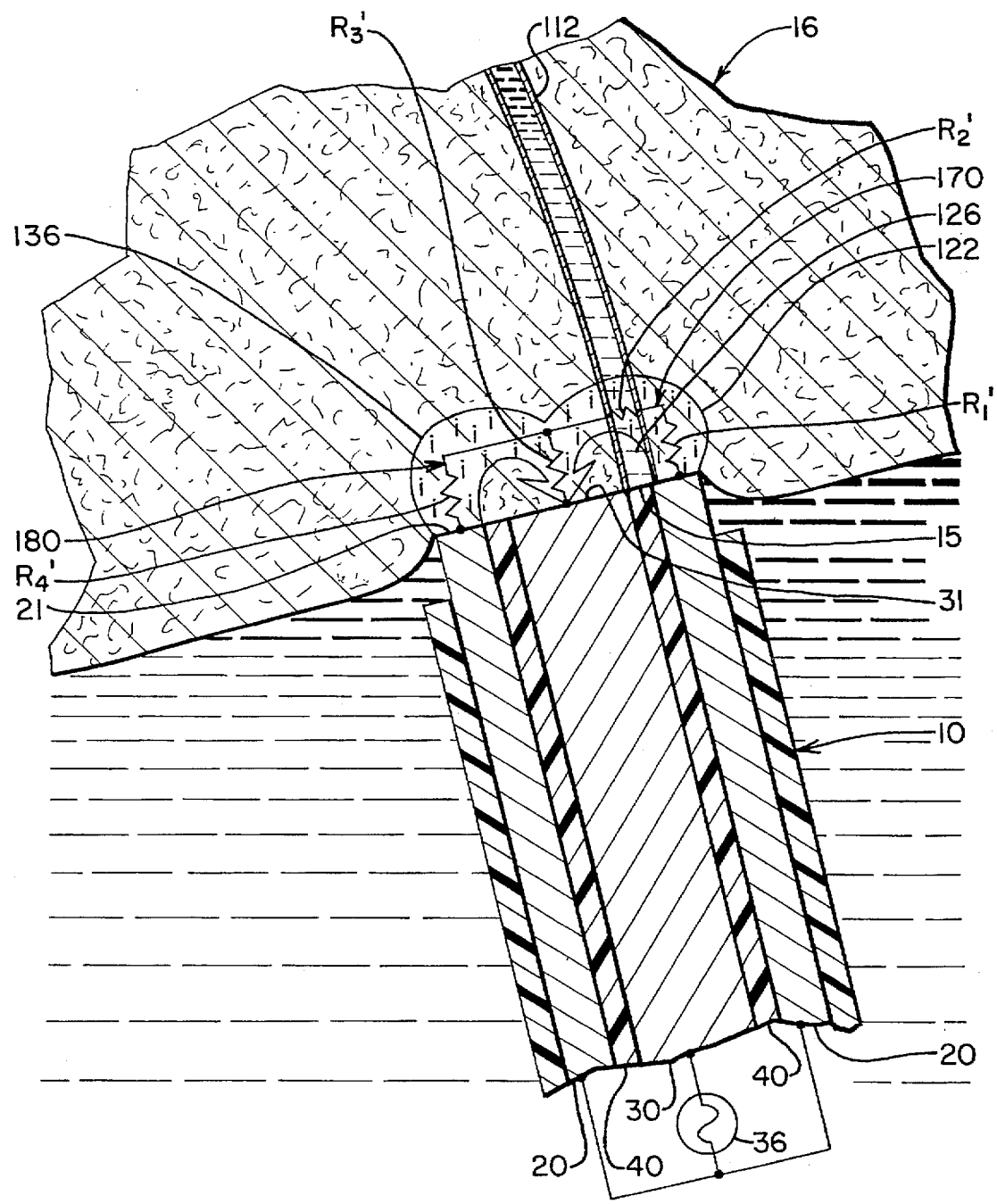
FIG. 6 is an enlarged cross-sectional view of the distal end of the probe in an orientation that is closer to normal to the tissue as it is sometimes to coagulate bleeders, especially smaller bleeders that can be accommodated between the distal ends of the inner electrode and the outer electrode.

In an alternative application, which works especially well for smaller damaged blood vessels or bleeders 112, as illustrated in FIG. 6, the distal ends 21, 31 of the respective outer electrode 20 and inner electrode 30 are both positioned in contact with the tissue 16, preferably, but not necessarily, with the bleeding area 115 of the small bleeder 112 approximately between the distal end 21 of the outer electrode 20 and the distal end 31 of the inner electrode 30. In this position, current flows between the outer electrode 20 and the inner electrode 30 in a path represented by arrow 122 through the blood vessel 12 as well as through the rest of the tissue 16 that is adjacent the probe 10 as represented by arrow 136. The current path indicated by arrow 122 between the outer electrode 20 and the inner electrode 30 through the blood vessel 112 will usually have a higher current density than the remaining current path 136 through the tissue 16 due to the lesser resistance of the blood 126 in the blood vessel 112 as compared to the resistance of the surrounding tissue 16. This current distribution of paths 122, 136 through the tissue 16 and blood vessel 112 is actually circular and generally corresponding to the periphery of the distal end of the probe 10, which does not show well in the cross-section of FIG. 6, but which will be understood by persons skilled in the art, with the arrow 12 representing current flow through the blood vessel 112 and the tissue 16 that is adjacent the distal end of the probe 10.

As the blood vessel 112 adjacent the distal end of probe 10 shrinks, the blood 126 coagulates, and the tissue 16 in path 122 in desiccated and necroses, all due to heat from the current flow in path 122, the resistances in path 122 increased. These increasing resistances cause a shift in electric current from path 122 to path 136, thereby avoiding vaporization of the tissue 16, blood vessel 112, and coagulated blood 126 in path 122.

This current flow distribution of FIG. 6 can also be modeled as two parallel circuits 170, 180. The parallel circuit 170 comprises in series the resistance $R_1'$ through the tissue 16 one side of the bleeder 112, the resistance $R_2'$ through the blood 126, and the resistance $R_3'$ through the tissue on the other side of the bleeder 112 that is adjacent the distal end 31 of inner electrode 30. The parallel circuit 180 comprises in series the resistance $R_4'$ of the tissue 16 that is adjacent the distal end 21 of outer electrode 20 (other than the $R_1'$ portion of tissue 16) in series with the resistance $R_3'$ of the tissue 16 that is adjacent the distal end 31 of inner electrode 30. As described above, there is initially current flowing in both paths 122, 136 between the distal end 21 of outer electrode 20 and the distal end 31 of inner electrode 30. Therefore, in the model, there is current initially in both parallel circuits 170, 180. However, the resistance $R_2'$ of the blood 126 in bleeder 112 is less than the resistances $R_1'$, $R_3'$, and $R_4'$ through tissue 16.

Consequently, based on observation of probe 10 in operation, it appears that the sum of the resistances $R_1'$, $R_2'$, and $R_3'$ in parallel circuit 170 is less than, or at least not substantially more than, the sum of the resistances $R_4'$ and $R_3'$ in parallel circuit 180.

Therefore, it appears that there is initially a higher current density in the parallel circuit 170 than in the parallel circuit 180 and that this higher current density causes initially more heat in the path 122. Also based on observation of the probe 10 in operation, it appears that this initial heat in path 122 desiccates and shrinks the blood vessel 112 as it desiccates and coagulates blood 126 and desiccates and necroses tissue 16 adjacent the distal ends 21, 31 of outer electrode 20 and inner electrode 30, which not only stems the flow of blood 126 from the bleeder 112, but also increases resistances $R_1'$, $R_2'$ and to some extent $R_3'$ in parallel circuit 170. This increase in resistances $R_1'$, $R_2'$ and $R_3'$ in circuit 170 causes more of the current to shift and flow through circuit 180, thus self-limiting the current flow in circuit 170 and the heat creation in the path 122 after the hemostasis of the bleeder 112.

The current shift to circuit 180 will also increase heat in path 136 and cause desiccation and necrosis of the tissue 16 in near path 136. However, depth of such desiccation and necrosis into the tissue 16 is limited to the tissue 16 within a distance from the distal end of probe 10 that is generally less than the diameter of the outer electrode 20. This limited depth is due to the fact that the current will not continue to extend over farther into tissue 16 as the tissue 16 adjacent the probe 10 is desiccated and necrosed. On the contrary, when the current has to travel through less distance of desiccated and necrosed tissue to get from the outer electrode 20 to the inner electrode 30 than to get to raw tissue 16, the current will no longer flow to such additional depths of raw tissue, but will take instead that path of least resistance through the desiccated and necrosed tissue that is adjacent the probe 10. Further, while the desiccated and necrosed tissue is more resistive or has more impedance than raw tissue 16, it will still not get so hot as to vaporize the desiccated and necrosed cells, unless that power is turned excessively high. Again, the goal is to desiccate and shrink bleeder vessels 112, desiccate and coagulate blood 126, and, if necessary, desiccate and necrose some small amount of tissue 16 immediately surrounding the bleeder 112 in order to achieve hemostasis, but not to vaporize cells or to carbonize cells. It is counter productive to vaporize or carbonize cells, because vaporization does not stop bleeding effectively, and carbonation of cells inhibits healing.

Figure 7:
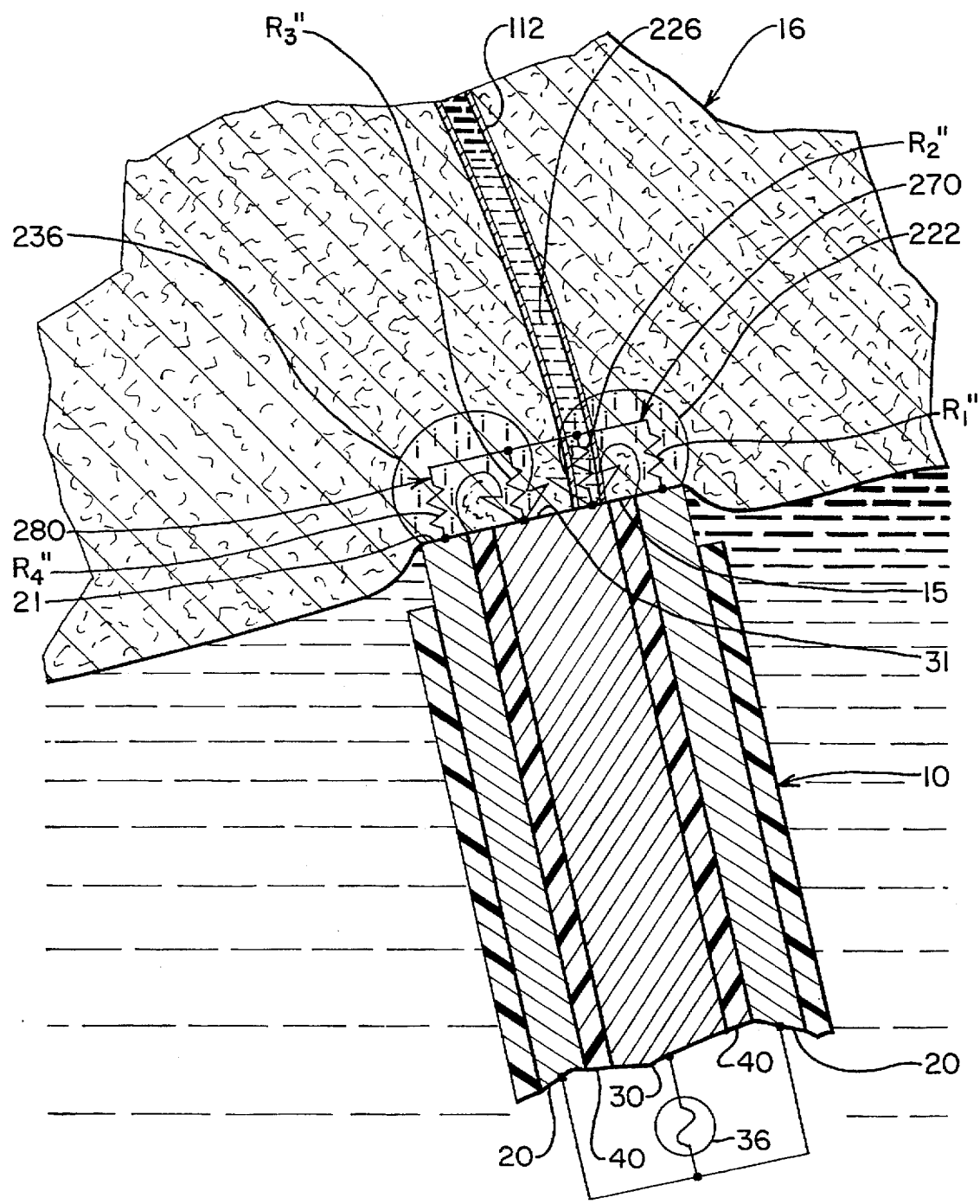
FIG. 7 is an enlarged cross-sectional view of the probe in an orientation similar to FIG. 6, but with the bleeder positioned more in contact with the distal end of the inner electrode.

The alternative application of probe 10 for hemostasis of a bleeding blood vessel 212 according to the present invention, as illustrated in FIG. 7, is not preferred, but it does work. This application is similar to that of FIG. 6, except inner electrode 30 is positioned directly on the bleeding blood vessel 212. In this application, the initial current path 222 includes the less resistive blood 226 in blood vessel 212, represented in the model by resistance $R_2"$, as well as some of the tissue 16 that is adjacent the distal end of the probe 110, represented by the resistances $R_1"$, $R_3"$ and $R_4"$. Therefore, based on observation of the probe 110 in operation, initial desiccation and shrinkage of blood vessel 212, coagulation of blood 226, and necrosing of tissue 16 adjacent the distal end of probe 10 combine to achieve hemostasis. Then, because resistances of desiccated, coagulated, and necrosed cells increase, current will shift to flow directly through raw tissue 16 between the distal end 21 of outer electrode 20 and distal end 31 of inner electrode 30, as illustrated by arrow 236. Again, as described above for the FIG. 6 application, depth of desiccation and necrosis of tissue 16 will generally not exceed the diameter of the outside electrode 20.

For all of the embodiments illustrated and described above, it is important for the purposes of this invention to size and proportion the exposed potions of the outer electrode 20 and inner electrode 30 such that the probe 10 is truly bipolar. For the purposes of this invention, bipolar means that it is possible for both the outer electrode 20 and the inner electrode 30 to be surgically active, even though they might not both always be actually surgically active means that sufficient heat is produced in cells at or immediately adjacent the electrode to alter cells physically, such as desiccation, coagulation, necrosis, ablation, vaporization, carbonization and the like. Therefore, to be truly bipolar for purposes of this invention, the probe 10 must be capable of causing such surgical activity in tissue and/or blood cells at or immediately adjacent both the outer electrode 20 and the inner electrode 30.

In dual electrode surgical systems where there is an electric potential between two electrodes and current passes between the two electrodes, there will tend to be significant heating at or adjacent only one of the electrodes when the ratio of the respective electrode surface areas is about ten to one (10:1) or higher. The electrode with the smaller surface area will have proportionately higher current density than the electrode with the larger surface area and will heat to the point that its contact impedance increases dramatically. Therefore, when the ratio of the electrode surface areas of the respective electrodes is about 10:1 or greater, as mentioned above, it becomes virtually impossible to flow enough current through the electrode with the larger surface area at a current density high enough to heat tissue adjacent the larger electrode to above about 50° C., which is the temperature at which tissue effects or surgical activity begins. At about 100° C., cells explode and vaporize, and carbonization occurs at about 200° C. Therefore, to be truly bipolar for purposes of this invention, the surface area of either electrode must be less than about ten times as large as the surface area of the other electrode to keep the ratio of the respective surface areas less than about 10:1.

In the surgical probe preferred embodiment 10 of this invention, where the distal ends 21, 31 of outer electrode 20 and inner electrode 30, respectively, are substantially coplanar and a peripheral surface 22 of outer electrode 20 extends beyond the outer insulation 42, as described above and shown in FIGS. 2–5, the surface area of the outer electrode 20 is effectively the sum of the respective uninsulated surface areas of the peripheral surface 22 and the distal end 21 of the outer electrode 20.

The surface area of the inner electrode 30 is essentially the uninsulated surface area of the distal end 31 of inner electrode 30. If the distal end 31 of the inner electrode 30 should also extend slightly beyond the inner insulation, as mentioned above, then the surface area of the inner electrode 30 would also include any additional uninsulated surface area of the periphery of the inner electrode 30 for purposes of the 10:1 ratio of respective surface areas of electrodes described above.

As also mentioned above, providing effective uninsulated surface areas of outer electrode 20 and inner electrode 30 within the 10:1 ratio described above does not mean that surgical activity occurs at or immediately adjacent both the outer electrode 20 and the inner electrode 30 at all times. For example, in the preferred embodiment and application illustrated in FIGS. 2–5, the distal end of the inner electrode 30 is spatially removed from the tissue 16, so there is no actual surgical activity strictly at the inner electrode 30 while desiccation, shrinking, coagulation, and necrosis in the blood vessel 12, blood 26, and tissue 16 occurs, as described above. Also, when most or all of the current flow shifts to flow through the fluid 28 in path 36 instead of paths 24, 32 after coagulation of flood 26 and necrosis of tissue 16 occurs, as described above, such surgical activity stops also at and near outer electrode 20. Similarly in the FIGS. 6 and 7 applications, electric current densities may shift or spread to paths that cause no further surgical activity at some or all areas at or adjacent one or both electrodes 20, 30 according to this invention. However, to achieve these self-selecting current paths and self-limiting surgical activities according to this invention, the probe 10 must be bipolar as described above.

The specific length of the exposed surface 22 of outer electrode 20 is not critical as long as the respective electrode surface areas of outer electrode 20 and inner electrode 30 remain within the 10:1 ratio for bipolarity described above. A range of 0.5 mm to 10 mm, for example, may be used to accommodate surgeon preference. The shorter the length, the more focused the electrical current path 24 will be; therefore, less overall tissue necrosis. Exposing more of the metal surface 22 of outer electrode 20 results in defocusing the current path 24 and will result in additional tissue necrosis beyond the bleeding point, but also avoids excessive current density that could vaporize tissue.

The diameter of the probe 10 is preferred in the range of 3.0–10.0 mm with the inner electrode 30 being about 1–2 mm diameter and the outer electrode 20 being about 2.5–5.0 mm diameter. The inner insulation 40 is preferably in the range of about 0.2 to 3 mm thick and the outer insulation is preferably in the range of about 0.2–3 mm thick. The length of the probe 10 should be long enough to extend through an incision or cannula to reach any desired location in the shoulder or knee joint. It is also preferred, but not necessary, that the RF current supply is approximately three-hundred (300 KHz) to three megahertz (3 MHz) and, optimally, the RF current supply is approximately five-hundred kilohertz (500 KHz). The power should be in the range of about twenty to one-hundred watts and is preferably in the range between forty and seventy watts into a load impedance in the range of about 25–1000 ohms preferably about 50–250 ohms, for example, 100 ohms to achieve the desired desiccation and shrinking of blood vessels, coagulation of blood, and necrosis of tissue as described above along with the self-selective current paths and self-limiting of surgical activity according to this invention.

Figure 8:
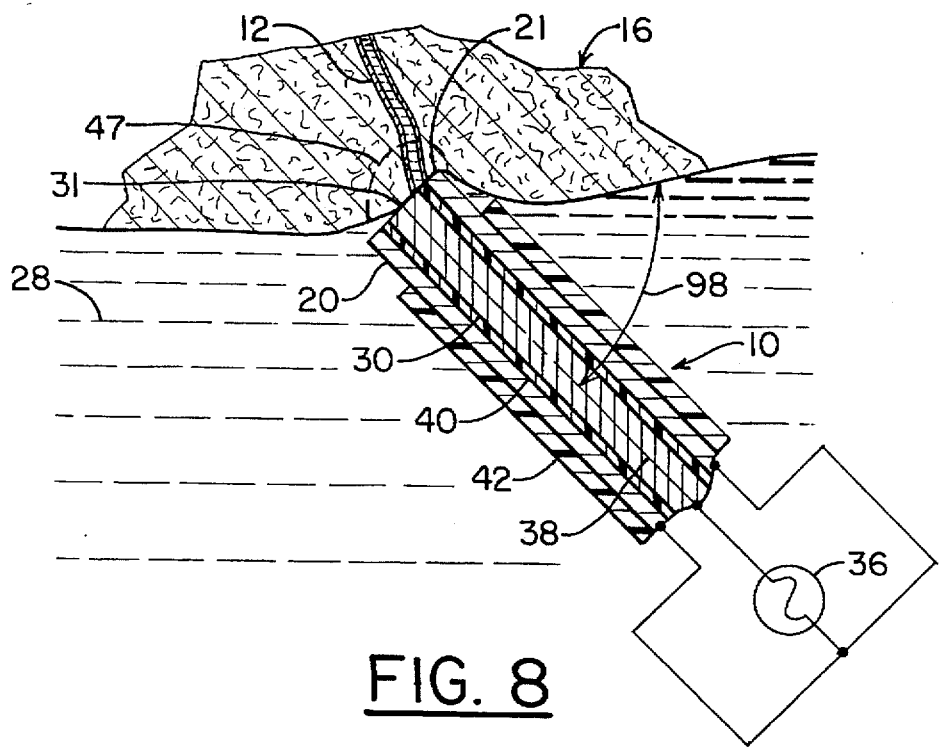
FIG. 8 is a cross-sectional view of the probe 10 oriented at an angle to the tissue surface.

The circular cross-section of probe 10 with the outer electrode 20 positioned concentrically around the inner electrode 30 has advantages, such as being equally effective regardless of the rotational position of the probe about its longitudinal axis 38 in relation to the tissue 16, as mentioned above. This configuration also accommodates variations in angles of the longitudinal axis 38 with the surface of the tissue 16 very easily. For example, the probe 10 is shown in FIG. 8 with its longitudinal axis 38 at about a 45° angle 98 with the surface of the tissue 16 adjacent the bleeder 12 and with the distal ends 21, 31 of the outer electrode 20 and the inner electrode 30 pushed into the tissue 16 enough to deform the tissue 16 at the surface where the bleeder is injured. In this orientation and variations of this orientation, part, but not all, of the distal end 21 of outer electrode 20 can be placed in contact with tissue 16, depending on how much electric contact area, thus current density, the surgeon wants or needs to coagulate the bleeder 12 and necrose just enough tissue 16 around the damaged bleeder 12, as indicated by phantom lines 47 to stem the bleeding. The larger the angle 98 and/or the more the surgeon pushes the probe 10 into the tissue 16, the more of the surface area of the distal end 21 of outer electrode 20 will contact tissue 16. Of course, if the angle 98 is small enough to leave the inner electrode immersed in fluid 28 but not in contact with tissue 16, then the embodiment shown in FIGS. 2–5 prevails and operates as described above.

Figure 9:
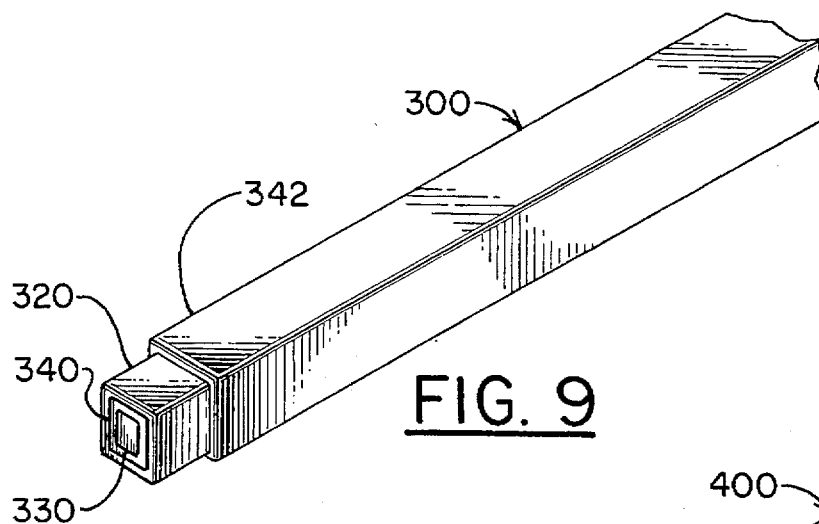
FIG. 9 is a perspective view of an alternate probe configuration of this invention.
Figure 10:
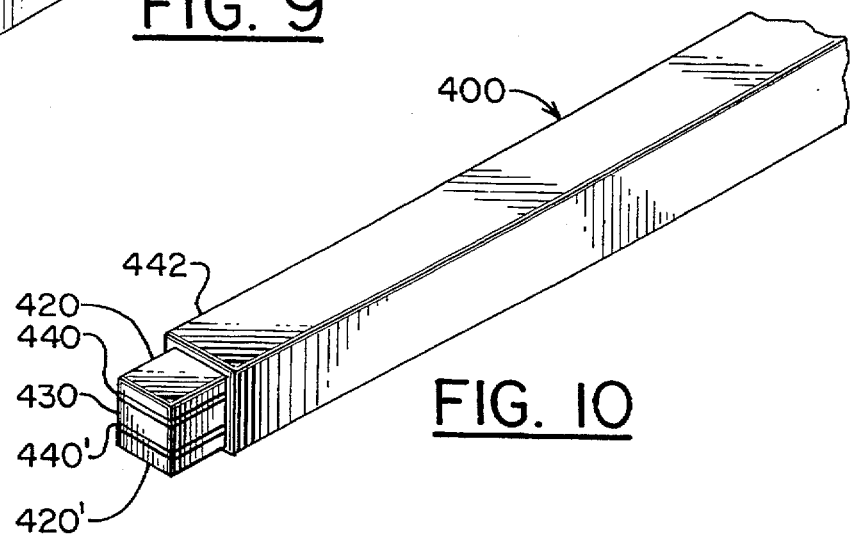
FIG. 10 is a perspective view of another alternate probe configuration of this invention.

The cross-section of the probe does not have to be circular, however. For example, an alternate probe 300 with a square cross-section of concentric inner electrode 330, inner insulation 340, outer electrode 320, and outer insulation 342, as shown in FIG. 9 can be used according to this invention. Other cross-sectional configurations, such as oval, polygonal, or other shapes can also be used. It is also not necessary for the electrodes to be concentric. For example, the probe 400 shown in FIG. 10 has an inner electrode 430 sandwiched between two outer electrodes 420, 420' with respective inner insulation layers 440, 440' intervening. The two outer electrodes 420, 420' can be, but are not necessarily at the same electrical potential as each other. The outer insulation 442 surrounds all of the electrodes. Many other variations of the invention are also possible to provide the bipolar surgical activity within the surface area ratios and exposed outer electrode parameters described above.

The foregoing description is considered as illustrative only of the principles of the invention. Furthermore, since numerous modifications and changes will readily occur to those skilled in the art, it is not desired to limit the invention to the exact construction and process shown and described above. For example, disposable and reusable versions of the probe 10 can be made according to the principles of the present invention. Accordingly, all suitable modifications and equivalents may be resorted to falling within the scope of the invention as defined by the claims which follow.

The embodiments of the invention in which an exclusive property or privilege is claimed are defined as follows:

1. A method of stemming flow of blood from a bleeding blood vessel in connective tissue of a joint that has been damaged during arthroscopy in an intra-articular space filled with an electrically conductive fluid, comprising:

inserting into the intra-articular space an elongated probe with a distal end and having an inner electrode at the distal end, an outer electrode at the distal end spaced radially outward from the inner electrode, an inner electrical insulation layer interposed between the inner electrode and the outer electrode extending to the distal end of the elongated probe, and an outer electrical insulation sleeve that does not extend to the distal end of the elongated probe such that a peripheral surface of the outer electrode adjacent the distal end is not covered by the outer electrical insulation sleeve and such that uninsulated surface area of the outer electrode is less than ten (10) times larger than uninsulated surface area of the inner electrode;

positioning the distal end of the probe adjacent the bleeding blood vessel with a portion of the peripheral surface of the outer electrode that is not covered by the outer electrical insulation sleeve in contact with both the connective tissue adjacent the bleeding blood vessel and the electrically conductive fluid and with the uninsulated surface area of the inner electrode in contact with the electrically conductive fluid spaced a distance apart from the bleeding blood vessel and connective tissue; and applying an RF voltage across said outer electrode and said inner electrode to cause electric current to flow through connective tissue, through the bleeding blood vessel, and through the electrically conductive fluid adjacent the outer electrode and inner electrode until sufficient heat is generated by the electric current to dessicate cells in the bleeding blood vessel and in connective tissue adjacent the bleeding blood vessel to stem flow of blood from the bleeding blood vessel.

2. The method of claim 1, wherein said electrically conductive fluid is a saline fluid.

3. The method of claim 2, wherein said saline fluid is a normal saline fluid.

4. The method of claim 1, including the step of applying said RF current and voltage in the range of about 20–100 watts.

5. The method of claim 4, wherein said RF current and voltage are applied in a range of about 40–70 watts.

6. The method of claim 1, including the step of applying said RF current in the range of about 300–3,000 KHz.

7. The method of claim 6, including the step of applying said RF current at about 500 KHz.

8. The method of claim 1, including providing said outer electrode positioned concentric with said inner electrode with inner electrical insulation layer positioned between said outer electrode and said inner electrode.

9. The method of claim 8, including providing said inner electrode in a form of a solid, elongated rod and providing said outer electrode in a form of an elongated tube.

10. The method of claim 9, including providing said elongated tube in a form of a cylinder with a polygonal cross-section.

11. The method of claim 9, including providing said elongated tube in a form of a cylinder with a polygonal cross-section.

12. The method of claim 8, including providing said outer electrode in an elongated shape with a distal end and providing said inner electrode in an elongated shape with a distal end such that said distal end of said outer electrode extends as least as far longitudinally as said distal end of said inner electrode.

13. Bipolar surgical probe apparatus for stemming blood flow from a blood vessel in connective tissue that has been damaged during arthroscopy in an intra-articular space of a joint that is filled with an electrically conductive fluid, said bipolar surgical probe apparatus comprising:

- an inner electrode that terminates at an inner electrode distal end with a flat surface area that defines a distal end plane;
- an elongated outer electrode that surrounds and extends coaxially with said elongated inner electrode to an outer electrode distal end with an outer electrode distal end surface area that is positioned in said distal end plane;
- an inner electrical insulation layer interposed between and in contact with both the inner electrode and the outer electrode and extending to said distal end plane such that said inner electrode is exposable electrically to said electrically conductive fluid only at said flat surface area in said distal end plane; and
- an outer electrical insulation sleeve surrounding said outer electrode, but not extending to said distal end plane, such that said outer electrode has an uninsulated peripheral surface area and such that, on the outer electrode, only said uninsulated peripheral surface area and said outer electrode distal end surface area are exposable electrically to said electrically conductive fluid with said uninsulated surface area and said outer electrode distal end surface area of said outer electrode together being less than about ten (10) times larger than said flat surface area of said inner electrode distal end.

14. The bipolar probe apparatus of claim 13, wherein said length of exposed peripheral surface of the outer electrode is in the range of 0.5–10 mm.

15. The apparatus of claim 13, wherein said outer insulation sleeve, said outer electrode, said inner insulation layer, and said inner electrode are all concentric to form an elongated, co-axial probe.

16. The bipolar probe of claim 15, wherein said elongated co-axial probe has a length and said outer electrode and said inner electrode both extend substantially for said length of said co-axial probe and both comprise a malleable, electrically conductive metal or alloy.

17. The bipolar probe apparatus of claim 6, wherein said outer electrode and said inner electrode both comprise aluminum.

18. The bipolar probe apparatus of claim 15, wherein said elongated co-axial probe has a longitudinal axis and said distal end plane is perpendicular to said longitudinal axis.

19. The bipolar probe apparatus of claim 13, wherein said inner electrode has a circular cross-section.

20. The bipolar probe apparatus of claim 13, wherein said outer electrode has a circular ring cross-section.

21. The bipolar probe apparatus of claim 13, wherein said outer electrode has a polygonal ring cross-section.

* * * * *